United States Patent
Brink

(10) Patent No.: US 9,310,245 B2
(45) Date of Patent: Apr. 12, 2016

(54) INTEGRATED SENSING DEVICE FOR ASSESSING INTEGRITY OF A ROCK MASS AND CORRESPONDING METHOD

(75) Inventor: Abraham Van Zyl Brink, Fochville (ZA)

(73) Assignee: CSIR, Pretoria (ZA)

(*) Notice: Subject to any disclaimer, the term of this patent is extended or adjusted under 35 U.S.C. 154(b) by 358 days.

(21) Appl. No.: 13/260,692

(22) PCT Filed: Oct. 25, 2010

(86) PCT No.: PCT/IB2010/054821
§ 371 (c)(1),
(2), (4) Date: Sep. 27, 2011

(87) PCT Pub. No.: WO2011/051874
PCT Pub. Date: May 5, 2011

(65) Prior Publication Data
US 2012/0200713 A1 Aug. 9, 2012

(30) Foreign Application Priority Data

Oct. 28, 2009 (ZA) .................................. 09/07561

(51) Int. Cl.
| | | |
|---|---|---|
| *G01H 3/10* | (2006.01) | |
| *G01H 3/08* | (2006.01) | |
| *G01N 25/72* | (2006.01) | |
| *G01N 29/04* | (2006.01) | |
| *G01V 9/00* | (2006.01) | |

(52) U.S. Cl.
CPC .................. *G01H 3/08* (2013.01); *G01N 25/72* (2013.01); *G01N 29/045* (2013.01); *G01V 9/005* (2013.01); *G01N 2291/0232* (2013.01)

(58) Field of Classification Search
CPC ........ G01H 3/08; G01N 25/72; G01N 29/045; G01N 2291/0232; G01V 9/005
See application file for complete search history.

(56) References Cited

U.S. PATENT DOCUMENTS

| 3,761,713 A | 9/1973 | Merrill |
| 2003/0216895 A1* | 11/2003 | Ghaboussi et al. ............... 703/2 |

(Continued)

FOREIGN PATENT DOCUMENTS

| EP | 1 918 698 | 5/2008 |
| WO | WO 2009060392 | 5/2009 |

OTHER PUBLICATIONS

Arai et al. (JP 2003-344121 A English Translation).*

(Continued)

*Primary Examiner* — Joseph Ustaris
*Assistant Examiner* — Jill Sechser
(74) *Attorney, Agent, or Firm* — Workman Nydegger

(57) ABSTRACT

A method of assessing the integrity of a rock mass, the method including receiving a thermal assessment of the integrity of a rock mass, receiving an acoustic assessment of the integrity of a rock mass and correlating the thermal- and acoustic assessments to obtain a combined assessment of the integrity of a rock mass. The invention also covers an assessment apparatus for assessing the integrity of a rock mass, which includes acoustic assessment means operable to provide an acoustic assessment of the integrity of a rock mass, thermal assessment means operable to provide a thermal assessment of the integrity of a rock mass and correlation means for correlating the acoustic assessment of the integrity of a rock mass with the thermal assessment of the integrity of a rock mass.

36 Claims, 2 Drawing Sheets

(56) References Cited

U.S. PATENT DOCUMENTS

Figure 1:
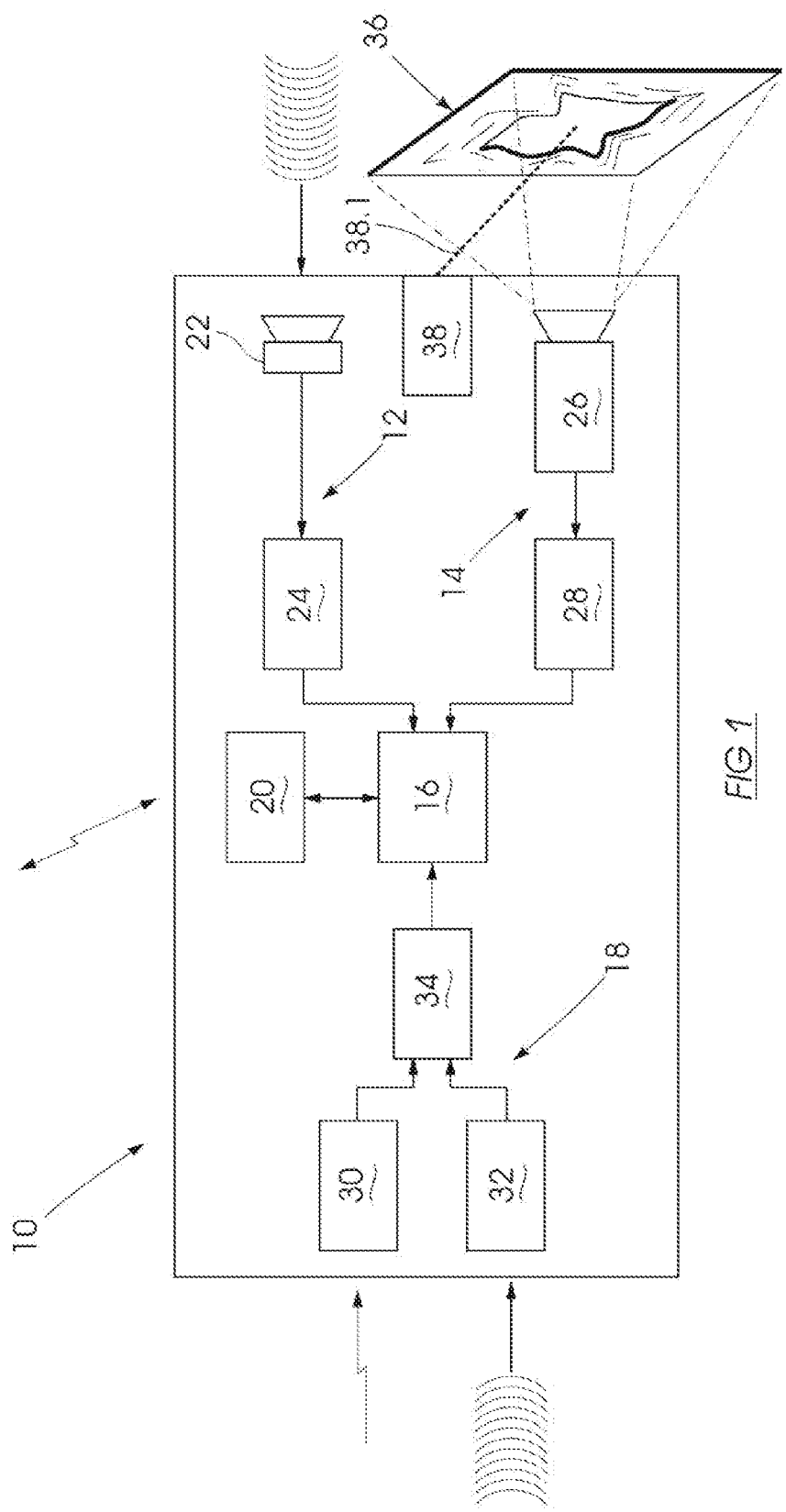

| | | | |
|---|---|---|---|
| 2004/0089812 A1* | 5/2004 | Favro et al. | 250/341.6 |
| 2007/0056374 A1* | 3/2007 | Andrews | 73/628 |
| 2007/0205886 A1* | 9/2007 | Huseth et al. | 340/539.15 |
| 2008/0137105 A1* | 6/2008 | Howard et al. | 356/630 |
| 2010/0045513 A1* | 2/2010 | Pett et al. | 342/25 C |
| 2010/0086174 A1* | 4/2010 | Kmiecik et al. | 382/103 |
| 2010/0224368 A1* | 9/2010 | Mason | 166/302 |
| 2010/0225541 A1* | 9/2010 | Hertzog et al. | 342/387 |
| 2011/0095757 A1* | 4/2011 | Nielsen et al. | 324/303 |

OTHER PUBLICATIONS

Khandelwal, et al. "Prediction of Blast-Induced Ground Vibration Using Artificial Neural Network" (2009).*

Database Compendex [Online], Engineering Information, Inc., New York, NY, US, Jan. 2008 Zhao Y et al.: "Experimental study on precursory information of deformations of coal-rock composite samples before failure", XP002627576, Database accession No. E20081111147382 * abstract & Yanshilixue Yu Gongcheng Xuebao/Chinese Journal of Rock Mechanics and Engineering Jan. 2008 Academia Sinica; Institute of Rock and Soil Mechanics; Editorial Office CN, vol. 27, No. 2, Jan. 2008, pp. 339-346.

International Search Report and Written Opinion as cited in PCT/IB2010/054821, Mar. 23, 2011.

* cited by examiner

INTEGRATED SENSING DEVICE FOR ASSESSING INTEGRITY OF A ROCK MASS AND CORRESPONDING METHOD

This invention relates to an assessment of the integrity of a rock mass. In particular, the invention relates to a method, apparatus and arrangement for assessing the integrity of a rock mass. The rock mass may for instance be the hanging wall (or roof) or a sidewall in a mine working such as a haulage, panel or stope.

BACKGROUND OF THE INVENTION

Many underground injuries are caused by the detachment and falling of rock fragments from rock masses in mines, which are unstable. For this reason it is considered important to have a means whereby the integrity, i.e. the stability or otherwise, of a rock mass can be assessed before mine workers enter the mine working and are exposed to potential injury from falling rock fragments caused by underground shifts.

A technique which has been in use for many years to assess the integrity of a rock mass in a mine working, typically a hanging wall, involves tapping the rock mass with a hammer or with a sounding bar, also known as a pinch bar and listening to the sound generated and making an assessment of the integrity of the mass according to the sound which is heard. The sound which is heard is caused primarily by the acoustic wave generated through vibration of the rock mass and other sources, for example the sounding bar, in the surrounding environment. The sound has a unique frequency distribution which must be interpreted in order for a determination to be made of the integrity of the rock mass.

The inventor is aware of techniques used for providing objective acoustic assessments of the integrity of rock masses. These techniques are based on the automated analysis of the acoustic signals being generated by the so-called tapping of the rock mass. However, it is desirable to improve the quality of the objective assessment of the rock beyond acoustic measurement techniques.

The present invention aims to provide an improved method of identifying portions of a rock mass presenting an increased rock fall risk by combining acoustic assessment with other assessment techniques.

SUMMARY OF THE INVENTION

According to one aspect of the invention, there is provided a method of assessing the integrity of a rock mass, the method including
receiving a thermal assessment of the integrity of a rock mass;
receiving an acoustic assessment of the integrity of a rock mass; and
correlating the thermal- and acoustic assessments to obtain a combined assessment of the integrity of a rock mass.

The method may include the prior step of conducting both a thermal- and acoustic assessment of the rock face.

Conducting a thermal assessment of the integrity of a rock mass may include capturing at least one thermal image of a rock face. An infrared thermal imager may be used to capture at least one thermal image of the rock face. Conducting a thermal assessment of the integrity of a rock mass may include processing the at least one thermal image of the rock face. Image-processing algorithms may be implemented to process the thermal images.

Processing the thermal images of the rock face includes implementing the image processing algorithms to identify zones on a rock face where thermal differentials occur. Typically zones where thermal differentials occur may be indicative of compromised integrity of the rock mass.

The image-processing algorithms may be implemented to identify a segmented zone in which a thermal differential can be detected with respect to the surrounding area on the rock face.

In a mine where a temperature difference exists on the surface of a host rock and the surrounding air, a temperature differential can be observed between intact (solid) rock and loose rock, which is thermally decoupled from the host rock.

Processing the thermal images may include generating an electronic signal representative of the thermal integrity of the rock mass.

Conducting an acoustic assessment of the rock face may include tapping the rock and receiving acoustic feedback from the tapping.

Receiving acoustic feedback may include electronically analysing the returned acoustic signal and receiving an electronic signal representative of the integrity of the rock mass.

The method may include employing electronic acoustic analysis devices and generating an electronic signal representative of the acoustic integrity of the rock mass.

The method may include determining locations on the rock face at which both the thermal- and acoustic assessments of the integrity of the rock mass are to be taken.

The method may include determining the position with reference to fixed beacons.

The position may be determined by image processing techniques, such as image mosaicing techniques.

The method may include visually indicating a location at which the acoustic assessment is to be conducted following the thermal assessment of the rock face.

The location at which the acoustic assessment is to be conducted, may be indicated by projecting a laser beam or another light source onto the rock face to ensure that the thermal- and acoustic assessments are conducted at the same location on the rock face.

Correlating the thermal- and acoustic assessments to obtain a combined assessment of the integrity of the rock mass may be automated.

Correlating the acoustic- and thermal assessments of the rock face may include processing the electronic signals representative of the thermal- and the acoustic integrity of the rock mass.

Processing the electronic signals may include setting up an algorithm representative of any one of a decision tree, a neural network, or the like, to determine the integrity of the rock mass based on the combined acoustic- and thermal integrity of the rock mass.

According to another aspect of the invention, there is provided an assessment apparatus for assessing the integrity of a rock mass, the apparatus including
acoustic assessment means operable to provide an acoustic assessment of the integrity of a rock mass;
thermal assessment means operable to provide a thermal assessment of the integrity of a rock mass;
correlation means for correlating the acoustic assessment of the integrity of a rock mass with the thermal assessment of the integrity of a rock mass.

The apparatus may include locating means for determining the locations at which the acoustic- and thermal assessments have been conducted.

The locating means may include a position processor, for calculating the location of the apparatus with reference to fixed beacons.

The locating means may include an image processor, operable to mosaic images together and to calculate any one of the location of the apparatus and the orientation of the apparatus with reference to at least two contiguous images.

The position processor may include triangulation means for determining the position of the apparatus in two- or more degrees of freedom.

In one embodiment, the locating means may include a combined radio frequency—(RF) and acoustic receiver, operable to receive an RF signal and an acoustic signal from a remote combined RF- and acoustic transmitter.

In one embodiment, the position processor may be operable to determine the distance of the apparatus from the transmitter based on the signal delay between the RF and acoustic signals.

In another embodiment the position processor may be operable to make a relative determination of the position by determining the distance between contiguous images of the rock face. This may be implemented by so called image stitching or image mosaicing and the recognition of common control points or markers on the rock face.

The acoustic assessment means may include capturing means for electronically capturing an acoustic signal, and analysis means for analysing the acoustic signal.

The capturing means may be in the form of a sonic transducer for generating an electric signal representative of the captured acoustic signal.

The acoustic analysis means may be operable from the electronically captured acoustic signal to derive an acoustic assessment of the rock mass.

The acoustic analysis means may include a neural network to derive an acoustic assessment of the rock mass.

The acoustic analysis means may be operable to generate a digital output representative of the acoustic assessment of the rock mass.

The thermal assessment means may include a thermal imager for capturing a thermal image of the rock face, and thermal analysis means for analysing the thermal image. The thermal analysis means may be operable from the captured thermal image to derive a thermal assessment of the rock mass. The thermal analysis means may include an image processor, operable to process the thermal image and derive information representative of unstable rock conditions (such as loose rock fragments) from the image.

The image processor may include a neural network to derive a thermal assessment of the rock mass.

The correlation means may include a processor operable from the outputs of the acoustic analysis means and the thermal analysis means to derive an integrity of the rock mass.

The correlation means may be operable to associate the acoustic analysis and the thermal analysis with locations at which the assessments were conducted.

The apparatus may include a transmitter operable to transmit results of the integrity assessment of the rock mass from the assessment apparatus to a remote receiver.

It is to be appreciated that the acoustic processor, the image processor and the location processor may be combined in electronic hardware.

According to another aspect of the invention, there is provided an assessment arrangement for assessing the integrity of a rock mass, the assessment arrangement including
an assessment apparatus as described; and
at least three location beacons locatable in known positions, the assessment apparatus operable in conjunction with the location beacons to determine its location in two- or three-dimensional space.

The location beacons may be combined RF- and acoustic transmitters operable to transmit RF and acoustic signals to the assessment apparatus.

The invention will now be described, by way of example only with reference to the following drawing(s):

DRAWING(S)

Figure 2:
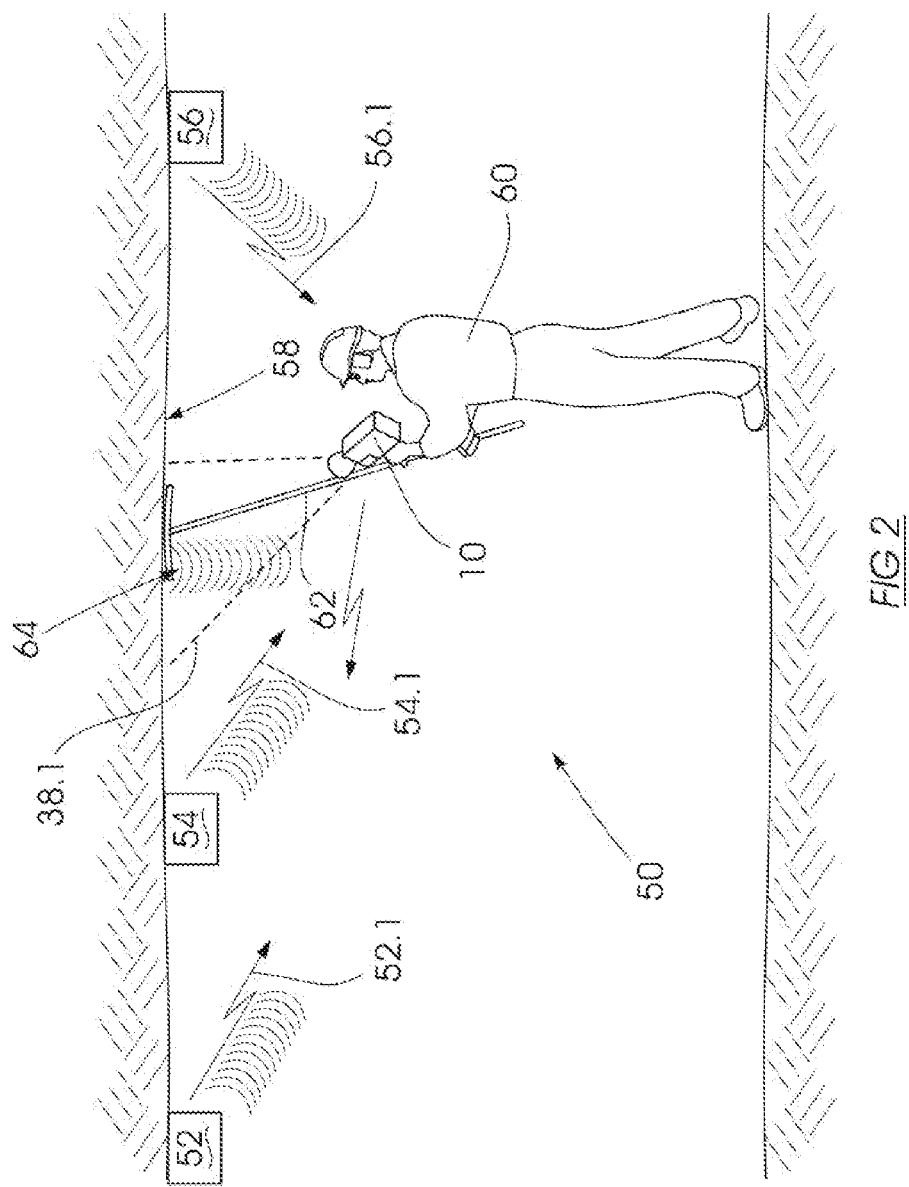

In the drawing(s):
FIG. 1 shows a block diagram of an assessment apparatus in accordance with the invention; and
FIG. 2 shows an assessment arrangement in accordance with the invention.

EMBODIMENT OF THE INVENTION

In FIG. 1 reference numeral 10 refers to an assessment apparatus in accordance with the invention.

The assessment apparatus 10 includes acoustic assessment means 12 and thermal assessment means 14, in operation to take acoustic- and thermal assessments of a rock face to determine the integrity of a rock mass.

The acoustic- and thermal assessment means 12, 14 are connected to correlation means 16 which is operable to correlate the acoustic assessment taken by the acoustic assessment means 12 with the thermal assessment taken by the thermal assessment means 14 and from the correlated assessments to compile an improved assessment of the integrity of the rock mass.

The assessment apparatus 10 further includes locating means 18, also connected to the correlation means 16 for providing a geographic location of the apparatus 10 at the position where an acoustic- and thermal assessment is taken.

The assessment apparatus 10 further includes a transceiver 20 connected to the correlation means 16. The transceiver 20 is operable to receive messages from a remote transceiver (not shown) and to transmit messages to the remote transceiver. In particular, the transceiver 20 is operable to transmit any data related to the integrity of the rock mass to the remote transceiver.

In the example shown, the acoustic assessment means 12 is in the form of a microphone 22 which can pick up a sound of a rock face when it is tapped with a sounding bar 62. The sound of the rock face is indicative of the integrity of the rock mass of which the rock face forms part. The microphone 22 is connected to an acoustic analysis processor 24 which is operable to receive the sound from the microphone 22 and then to perform analysis on the sound to provide an acoustic assessment of the integrity of the rock mass.

The thermal assessment means 14 includes a thermal imager 26 which can capture thermal images of a rock face 36. The thermal imager 26 is connected to thermal assessment means in the form of an image processor 28. The image processor 28 is operable to apply image processing algorithms on a captured image and to interpret the thermal image in terms of the integrity of the rock mass.

An output from the image processor 28 and an output from the acoustic analysis processor 24 are connected to the correlation processor 16. The correlation processor 16 correlate the output from the acoustic analysis processor 24 with the output from the image processor 28 to provide an assessment of the integrity of the rock mass based on both the acoustic- and thermal assessments.

The locating means 18 is in the form of a combined acoustic-/radio frequency (RF) position sensor. The locating means thus includes a radio frequency receiver 30 and an acoustic sensor 32, which are both connected to a position processor.

Outputs from the acoustic sensor and the RF receiver are combined into a position processor 34, which is operable from received acoustic-/RF signals to determine the relative position of the apparatus 10 in relation to a set of external acoustic-/RF transmitters/beacons (see FIG. 2). The position processor is operable to determine the distance of the apparatus 10 from the external acoustic-/RF transmitters based on the signal delay between the RF and acoustic signals. The position processor 34 is operable to identify received acoustic- and RF signals originating from an identified source. By receiving more than two sets of acoustic-/RF signals, the position processor 34 is operable to triangulate its position relative to each of the external acoustic-/RF transmitters. The position processor 34 then provides an output to the correlation processor 16 to record the relative position of the apparatus 10 when an acoustic and thermal assessment has been made.

The correlation processor 16 is operable via the transceiver 20 to transmit the acoustic- and thermal assessments in combination with the relative position of the apparatus 10.

In FIG. 2 an assessment arrangement 50 is shown with an assessment apparatus 10 and three external acoustic-/RF transmitters/beacons 52, 54, 56 mounted in known positions along a rock wall 58.

The acoustic-/RF transmitters 52, 54, 56 each transmit a combined acoustic-/RF signal pair 52.1, 54.1, 56.1, which can be received by the acoustic sensor 32 and RF receiver 30. The RF signals contains the identity of the transmitters 52, 54, 56, which is associated with a specific installation position. By receiving the signal pairs 52.1, 54.1, 56.1 the apparatus 10 can, through triangulation, determine its relative position in two dimensions to the three sensors 52, 54, 56. By associating the identities of the transmitters 52, 54, 56 with their installed positions, the apparatus can determine its position along the rock wall 58 in two or three degrees of freedom (i.e. its translation relative to the sensors 52, 54, 56.

In other embodiments, the processors 24, 28, 16, 34 can be combined in electronic hardware, depending on the hardware design of the apparatus 10.

In use a user 60 aims the apparatus 10 towards the rock face 58 to capture a thermal image of the rock face 58. The laser pointer 38 transmits a laser beam 38.1 to indicate the position on the rock face 58 where the rock is to be tapped. The user 60 taps the rock wall 58 with a sounding bar 62, and an acoustic signal 64 is generated and picked up by the microphone 22. The apparatus 10 takes an acoustic- and thermal assessment of the rock face 58 to determine the integrity of the rock mass.

The transceiver 20 transmits the acoustic- and thermal assessment of the rock mass with the location at which they were taken to a remote receiver (not shown).

The inventor believes that the invention as described provides a new and method and apparatus of determining the integrity of a rock mass.

The invention claimed is:

1. A method of assessing the integrity of a rock mass, the method including:
   receiving a thermal assessment of the integrity of the rock mass by detecting any segmented zones in the rock mass that are thermally decoupled from a host rock of the rock mass, the thermal assessment including:
      capturing a thermal image of a face of the rock mass while the face of the rock mass is in an ambient temperature condition; and
      identifying any segmented zones of loose rock within the rock mass, including segmented zones extending into the rock mass beyond the face of the rock mass, by detecting any temperature differential zones existing on the face of the rock mass while the face of the rock mass is in the ambient temperature condition;
   receiving an acoustic assessment of the integrity of at least a portion of the rock mass from which the thermal assessment was received; and
   correlating the thermal- and acoustic assessments to obtain a combined assessment of the integrity of at least the portion of the rock mass from which both thermal and acoustic assessments were received.

2. A method as claimed in claim 1, which includes the prior step of conducting both a thermal and acoustic assessment of the rock mass, the thermal assessment of the integrity of the rock mass including capturing at least one thermal image of a rock face by means of an infrared thermal imager and processing the at least one thermal image of the rock face.

3. A method as claimed in claim 2, in which image-processing algorithms are implemented to process the thermal images, by identifying zones on the rock face where thermal differential occur and to identify a segmented zone in which a thermal differential can be detected with respect to the surrounding area on the rock face.

4. A method as claimed in claim 3, in which processing the thermal images includes generating an electronic signal representative of the thermal integrity of the rock mass.

5. A method as claimed in claim 2, in which conducting an acoustic assessment of the rock mass includes tapping the rock and receiving acoustic feedback from the tapping.

6. A method as claimed in claim 5, in which receiving acoustic feedback includes electronically analysing the returned acoustic signal and receiving an electronic signal representative of the integrity of the rock mass.

7. A method as claimed in claim 6, which includes employing electronic acoustic analysis devices and generating an electronic signal representative of the acoustic integrity of the rock mass.

8. A method as claimed in claim 2, which includes determining geographic locations on the rock face at which both the thermal and acoustic assessments of the integrity of the rock mass are to be taken.

9. A method as claimed in claim 8, in which the geographic locations are determined with reference to fixed beacons.

10. A method as claimed in claim 8, in which the geographic locations on the rock face are determined by image processing techniques.

11. A method as claimed in claim 8, which includes visually indicating a geographic location on the rock face at which the acoustic assessment is to be conducted following the thermal assessment of the rock face.

12. A method as claimed in claim 11, in which the location at which the acoustic assessment is to be conducted, is indicated by projecting a laser beam onto the rock face to ensure that the thermal and acoustic assessments are conducted at the same location on the rock face.

13. A method as claimed in claim 2, in which correlating the thermal and acoustic assessments to obtain a combined assessment of the integrity of the rock mass is automated.

14. A method as claimed in claim 13, in which correlating the acoustic- and thermal assessments of the rock face includes processing the electronic signals representative of the thermal and the acoustic integrity of the rock mass.

15. A method as claimed in claim 14, in which processing the electronic signals includes setting up an algorithm representative of any one of a decision tree, a neural network, to determine the integrity of the rock mass based on the combined acoustic and thermal integrity of the rock mass.

16. An assessment apparatus for assessing the integrity of a rock mass, the apparatus including acoustic assessment means operable to directly measure sound and provide an acoustic assessment of the integrity of a rock mass;

thermal assessment means operable to provide a thermal assessment of the integrity of at least a portion of the rock mass from which the acoustic assessment was received, the thermal assessment means being configured to capture a thermal image of a face of the rock mass while the face of the rock mass is in an ambient temperature condition in order to identify any segmented zones in the rock mass that are thermally decoupled from a host rock of the rock mass, including segmented zones extending into the rock mass beyond the face of the rock mass; and correlation means for correlating the acoustic assessment of the integrity of the rock mass with the thermal assessment of the integrity of the rock mass for at least the portion of the rock mass from which both thermal and acoustic assessments were received.

17. An apparatus a claimed in claim 16, which includes locating means for determining the locations at which the acoustic and thermal assessments have been conducted.

18. An apparatus as claimed in claim 17, in which the locating means includes a position processor, for calculating the location of the apparatus with reference to fixed beacons.

19. An apparatus as claimed in claim 18, in which the locating means includes an image processor, operable to mosaic images together and to calculate any one of the location of the apparatus and the orientation of the apparatus with reference to at least two contiguous images.

20. An apparatus as claimed in any one of claim 18 and claim 19, in which the position processor includes triangulation means for determining the position of the apparatus in two- or more degrees of freedom.

21. An apparatus as claimed in claim 18, in which the locating means includes a combined radio frequency (RF) and acoustic receiver, operable to receive an RF signal and an acoustic signal from a remote combined RF- and acoustic transmitter.

22. An apparatus as claimed in claim 21, in which the position processor is operable to determine the distance of the apparatus from the transmitter based on the signal delay between the RF and acoustic signals.

23. An apparatus as claimed in claim 22, in which the acoustic assessment means includes capturing means for electronically capturing an acoustic signal, and analysis means for analysing the acoustic signal.

24. An apparatus as claimed in claim 23, in which the capturing means is in the form of a microphone for generating an electric signal representative of the captured acoustic signal.

25. An apparatus as claimed in claim 23, in which the acoustic analysis means is operable from the electronically captured acoustic signal to derive an acoustic assessment of the rock mass.

26. An apparatus as claimed in claim 25, in which the acoustic analysis means includes a neural network to derive an acoustic assessment of the rock mass.

27. An apparatus as claimed in claim 26, in which the acoustic analysis means is operable to generate a digital output representative of the acoustic assessment of the rock mass.

28. An apparatus as claimed in claim 16, in which the thermal assessment means includes a thermal imager for capturing a thermal image of the rock mass, and thermal analysis means for analysing the thermal image.

29. An apparatus as claimed in claim 28, in which the thermal analysis means is operable from the captured thermal image to derive a thermal assessment of the rock mass.

30. An apparatus as claimed in claim 29, in which the thermal analysis means includes an image processor, operable to process the thermal image and derive information representative of unstable rock conditions from the image.

31. An apparatus as claimed in claim 30, in which the image processor includes a neural network to derive a thermal assessment of the rock mass.

32. An apparatus as claimed in claim 16, in which the correlation means includes a processor operable from the outputs of the acoustic analysis means and the thermal analysis means to derive an integrity of the rock mass.

33. An apparatus as claimed in claim 16, in which the correlation means is operable to associate the acoustic assessment and the thermal assessment with locations at which the assessments were conducted.

34. An apparatus as claimed in claim 16, which includes a transmitter operable to transmit results of the integrity assessment of the rock mass from the assessment apparatus to a remote receiver.

35. An assessment arrangement for assessing the integrity of a rock mass, the assessment arrangement comprising:

an assessment apparatus comprising:
acoustic assessment means operable to directly measure sound and provide an acoustic assessment of the integrity of a rock mass;
thermal assessment means operable to provide a thermal assessment of the integrity of the rock mass, including means for identifying any segmented zones in the rock mass, including identifying segmented zones extending into the rock mass beyond the face of the rock mass, by capturing a thermal image of a face of the rock mass while the face of the rock mass is in an ambient temperature condition, and detecting any temperature differential zones existing on the face of the rock mass while the face of the rock mass is in the ambient temperature condition in order to identify any segmented zones of loose rock within the rock mass; and
correlation means for correlating the acoustic assessment of the integrity of the rock mass with the thermal assessment of the integrity of the rock mass; and at least three location beacons locatable in known positions, the assessment apparatus operable in conjunction with the location beacons to determine its location in two- or three-dimensional space.

36. An assessment arrangement as claimed in claim 35, in which the location beacons are combined RF- and acoustic transmitters operable to transmit RF and acoustic signals to the assessment apparatus.

* * * * *